(12) United States Patent
Hamano

(10) Patent No.: US 8,602,022 B2
(45) Date of Patent: Dec. 10, 2013

(54) MEDICINE EJECTION DEVICE AND CONTROL METHOD THEREFOR

(75) Inventor: Soji Hamano, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 763 days.

(21) Appl. No.: 12/812,477

(22) PCT Filed: Mar. 13, 2009

(86) PCT No.: PCT/JP2009/055548
§ 371 (c)(1),
(2), (4) Date: Jul. 12, 2010

(87) PCT Pub. No.: WO2009/116651
PCT Pub. Date: Sep. 24, 2009

(65) Prior Publication Data
US 2010/0282255 A1    Nov. 11, 2010

(30) Foreign Application Priority Data

Mar. 18, 2008    (JP) .................................. 2008-069720

(51) Int. Cl.
*A61M 11/00*    (2006.01)
(52) U.S. Cl.
USPC ............. 128/200.16; 128/200.23; 128/203.15
(58) Field of Classification Search
USPC ............. 128/200.16, 200.23, 203.15, 204.21, 128/204.22
See application file for complete search history.

(56) References Cited

U.S. PATENT DOCUMENTS

| | | | |
|---|---|---|---|
| 4,664,107 A | 5/1987 | Wass | 128/200.23 |
| 2007/0062520 A1 | 3/2007 | Nobutani et al. | 128/200.14 |
| 2008/0223362 A1 | 9/2008 | Hamano et al. | 128/200.23 |
| 2009/0050142 A1 | 2/2009 | Hamano | 128/200.34 |

FOREIGN PATENT DOCUMENTS

| | | |
|---|---|---|
| JP | 2004-283245 | 10/2004 |
| JP | 2004-290593 | 12/2004 |

OTHER PUBLICATIONS

Office Action issued Jul. 17, 2012 in counterpart Japanese Application 2008-069720, with translation.

*Primary Examiner* — Steven Douglas
(74) *Attorney, Agent, or Firm* — Fitzpatrick, Cella, Harper & Scinto

(57) ABSTRACT

Provided are a medicine ejection device capable of realizing appropriate ejection by surely setting an inner pressure of a medicine tank at a negative pressure in an initial period of every ejection time, and a control method for the medicine ejection device. A medicine container section that contains medicine is coupled to a medicine ejection section including nozzles from which the medicine is ejected, and elements which generate energy for ejecting the medicine from the nozzles. A plug as a movable wall positionally shifts so that a capacity of the medicine container section can increase or decrease in accordance with a predetermined pressure difference between an inside and outside of the medicine container section. Prior to opening a head cap, the capacity is increased so as to generate pressure variations in a negative pressure direction, which have a larger value than a value equivalent to the predetermined pressure difference.

4 Claims, 7 Drawing Sheets

MEDICINE EJECTION DEVICE AND CONTROL METHOD THEREFOR

TECHNICAL FIELD

The present invention relates to a medicine ejection device that is formed so as to be portably usable by a user, and is usable for an inhalation device for allowing the user to inhale medicine, and relates to a control method for the medicine ejection device.

BACKGROUND ART

An inhalation device that ejects fine liquid droplets of medicine into an air path, through which air inhaled through a mouthpiece flows, by using an ejection principle of an ink-jet method, and allows a user to inhale the ejected fine liquid droplets, has been developed (for example, refer to Japanese Patent Application Laid-Open No. 2004-290593 and Japanese Patent Application Laid-Open No. 2004-283245). Such an inhalation device has an advantage capable of spraying precisely a predetermined amount of the medicine in a uniformed particle size.

As basic components of such a medicine ejection device, there are an ejection head in which an ejection energy generation element such as a heater element is disposed, and a medicine tank that contains the medicine supplied to the ejection head.

In the case of preserving an amount of medicine equivalent to multiple inhalation actions in the medicine tank, it is necessary to prevent a concentration change and quality deterioration of the medicine every after use. Therefore, a configuration of atmospheric communication, which is usually used in an ink tank for use in an ink-jet printer, cannot be adopted for the medicine tank, and high gas barrier property and hermetic sealing property are required. The same also applies to the case that a medicine in which contact with air is not desirable is used.

In this case, a flexible container may be used as the medicine tank, and may be formed so as to collapse following to the ejection (Japanese Patent Application Laid-Open No. 2004-290593). For example, aluminum is evaporated onto a polyester film, whereby the medicine tank can be formed. Further, in a case where a body of the medicine tank is a glass container, the medicine tank may be formed in closing one end of the body with a rubber plug so as to be capable of reducing a capacity thereof following the ejection.

In such a configuration, the capacity of the container is increased and decreased when a pressure difference between an inside and outside of the container exceeds a predetermined value. For example, in a case of the glass container, when force applied to the plug owing to a negative pressure inside the tank exceeds the maximum static friction between the glass container and the plug, the plug begins to move in a direction to reduce the capacity of the medicine tank. On the contrary, in the case where a pressure in the tank is a positive pressure, the plug begins to move in a direction to increase the capacity.

Here, in the event of starting to eject the medicine, it is desirable that the pressure in the medicine tank be within an appropriate range. Description thereof is made in detail in the following. As the negative pressure in the medicine tank is increased, that is, as the pressure inside the tank becomes lower than the atmospheric pressure outside the tank, ejection performance from the ejection head is lowered. In the case of ejecting the medicine by means of a head with a nozzle diameter of 3 µm, an ejection amount thereof is not decreased until the negative pressure in the medicine tank becomes approximately −5 kPa. However, it has been understood that the ejection amount is reduced little by little when the negative pressure in the medicine tank exceeds this value, and when the negative pressure reaches −20 kPa, the medicine tank draws in the air from the ejection head, and becomes incapable of ejecting the medicine. On the contrary, in a state where the inner pressure of the tank is the positive pressure, there is a risk that liquid leakage may occur, and hence not desirable. Therefore, it has turned out that, in order to realize stable ejection, it is desirable that the inside of the medicine tank be surely set at the negative pressure from an initial period of the ejection, and that the negative pressure be maintained at a predetermined value or less as much as possible. The predetermined value is −5 kPa in the above-mentioned example.

However, owing to an environmental change while the device is not used, the pressure inside of the medicine tank in the event of starting the ejection sometimes becomes the positive pressure.

DISCLOSURE OF THE INVENTION

It is an object of the present invention to provide a medicine ejection device capable of realizing appropriate ejection by surely setting the inner pressure of the medicine tank at the negative pressure in an initial period of every ejection time, and to provide a control method for the medicine ejection device.

In view of the above-mentioned problem, the present invention provides a medicine ejection device comprising:

a medicine ejection section including ejection nozzles and an element that generates energy for ejecting medicine from the ejection nozzles;

a medicine container section that is coupled to the medicine ejection section and contains the medicine;

a movable wall that positionally shifts so that a capacity of the medicine container section can change in accordance with a predetermined pressure difference between an inside and outside of the medicine container section, the movable wall being provided to the medicine container section; and a pressure control unit for generating pressure variations in a negative pressure direction in an inside of the medicine container section, the pressure variations having a larger value than a value equivalent to the predetermined pressure difference, thereby ejecting the medicine.

Further, in view of the above-mentioned problem, the present invention provides a control method for a medicine ejection device which comprises:

a medicine ejection section including ejection nozzles and an element that generates energy for ejecting medicine from the ejection nozzles;

a medicine container section that is coupled to the medicine ejection section and contains the medicine; and a movable wall that positionally shifts so that a capacity of the medicine container section can change in accordance with a predetermined pressure difference between an inside and outside of the medicine container section, the movable wall being provided to the medicine container section, thereby ejecting the medicine, the control method comprising:

increasing the capacity of the medicine container section so as to generate pressure variations in a negative pressure direction in an inside of the medicine container section, the pressure variations having a larger value than a value equivalent to the predetermined pressure difference;

opening a protective member that protects the ejection nozzles; and driving the element to eject the medicine.

According to the medicine ejection device of the present invention, the inner pressure of the medicine tank is changed to the negative pressure direction by the predetermined amount prior to the ejection, and accordingly, the inside of the medicine tank can be surely set at the negative pressure. Therefore, there is no risk that the medicine may leak from the ejection nozzles in the event of starting the ejection.

Other features and advantages of the present invention are apparent from the following description taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention are now described in detail in accordance with the accompanying drawings.

In principle, the same reference symbols denote the same constituents, and description thereof is omitted.

(Medicine Ejection Device)

Figure 1:
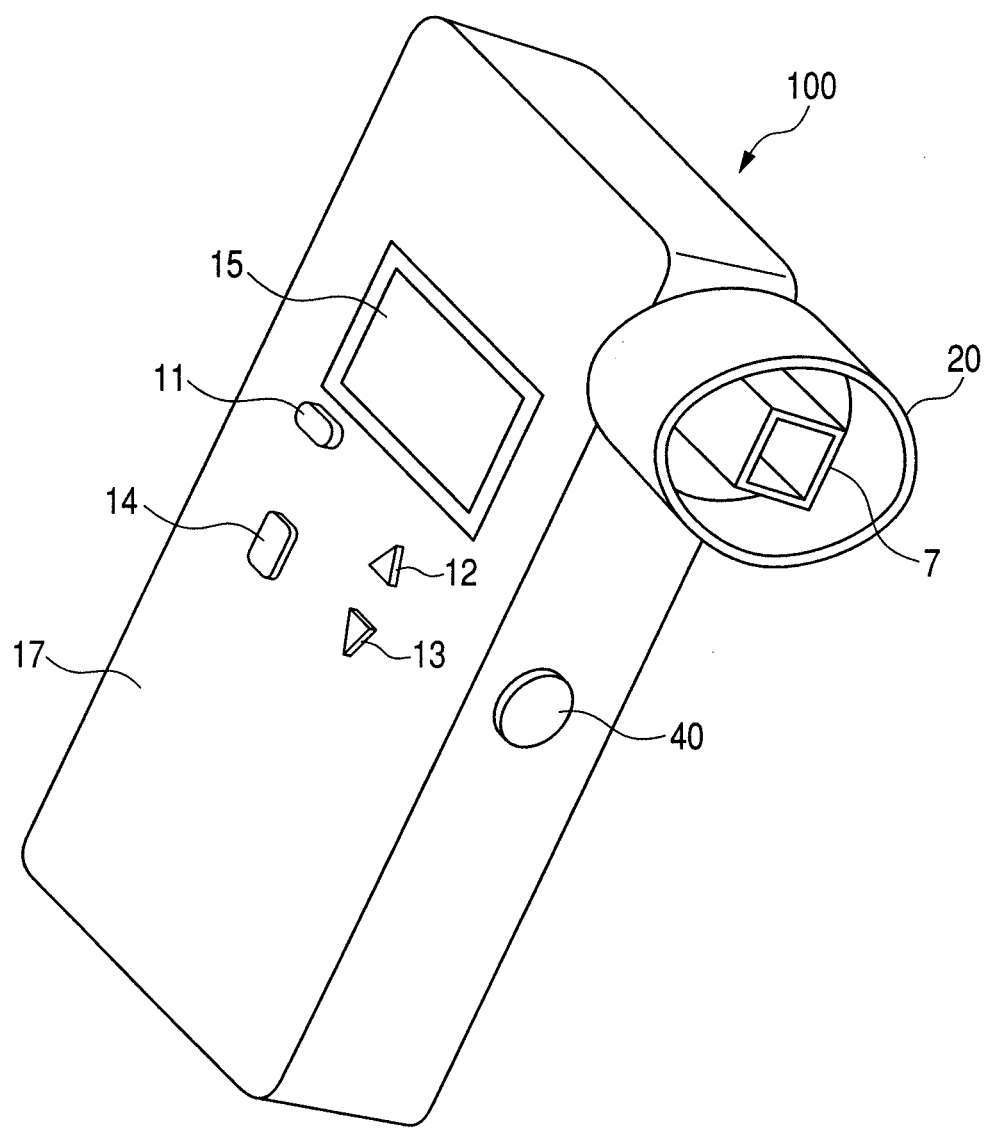
FIG. 1 is a perspective view of an example of a medicine ejection device of the present invention, illustrating an exterior appearance of an inhaler 100 that allows a user to inhale medicine.
Figure 2:
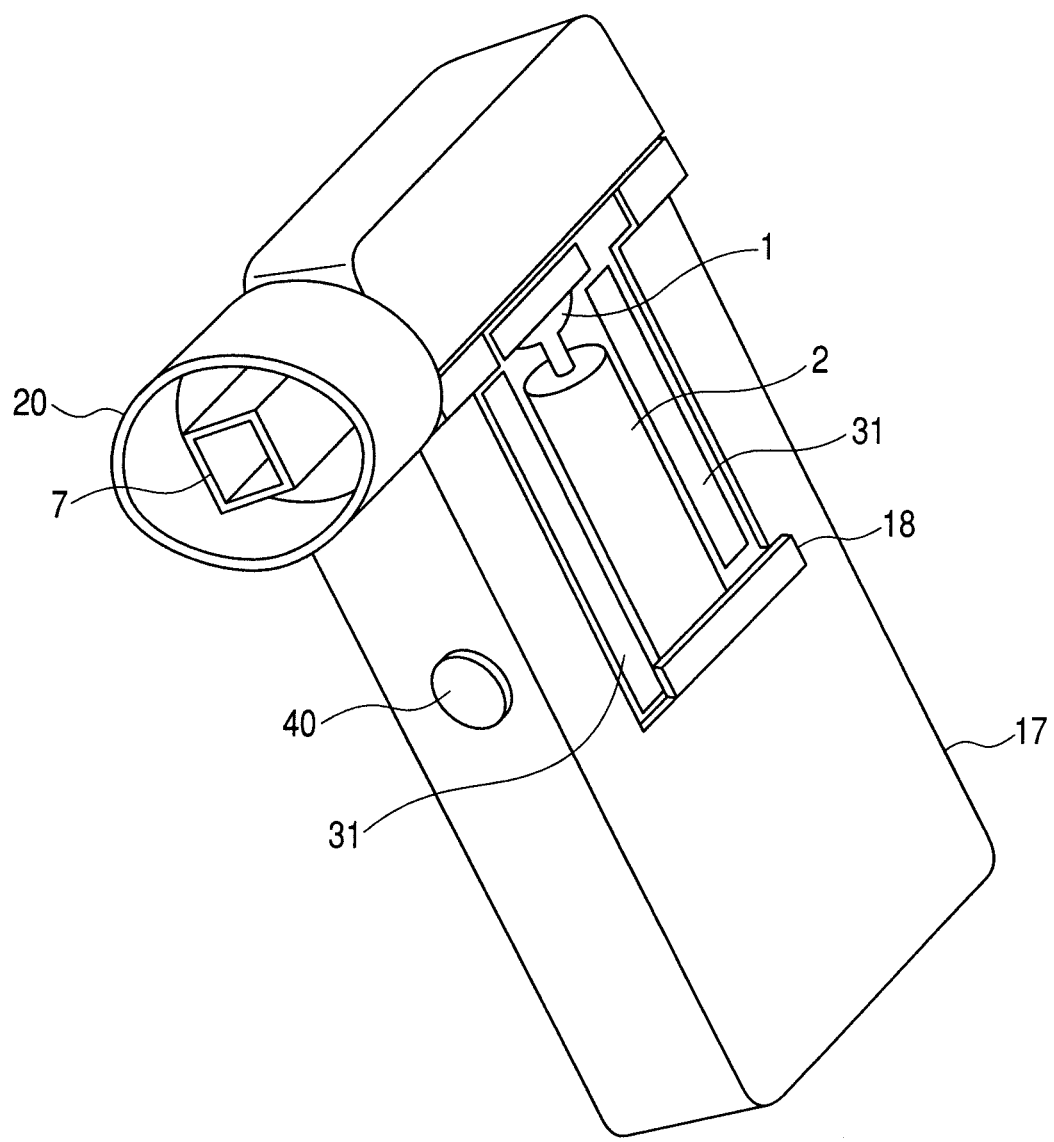
FIG. 2 is a perspective view illustrating a state where an access cover 18 is opened in the inhaler of FIG. 1.

FIG. 1 is a perspective view of an example of a medicine ejection device of the present invention, illustrating an exterior appearance of an inhaler 100 that allows a user to inhale medicine. A body exterior of the inhaler 100 is formed of a housing case 17 and an access cover 18 (FIG. 2). Reference numeral 40 denotes a lock release button of the access cover. Before pressing the button 40, the access cover 18 is locked so as not to be opened. At the time of opening the access cover 18, the release button 40 is pressed, whereby such locking of the access cover 18 is released. On the housing case 17, a display unit 15 for displaying a dosage, a time, an error, and the like is provided. Further, there are provided a menu switching button 11 for allowing the user to make a setting, an UP button 12, a DOWN button 13, and a DECISION button 14, which are setting buttons.

FIG. 2 illustrates a state where the access cover 18 is opened in the inhaler of FIG. 1. The access cover 18 is made slidable in a downward direction of the inhaler. When the access cover 18 is slid and housed in an inside of the body of the inhaler, there come into view an ejection head section 1 as a medicine ejection section made detachable from the body of the device, and a medicine tank 2 as a medicine container section. The ejection head section 1 ejects the medicine toward an air path 7. The user breathes in from an inhalation port (mouthpiece) 20, thus making it possible to inhale the medicine ejected into the air path 7. In this embodiment, the inhalation port 20 and the air path 7 are integrated with each other. The inhalation port 20 is thrown away every time when the inhalation is performed, or is reused after being washed after the inhalation. The ejection head section 1 and the medicine tank 2 are replaced when an amount of the medicine in the medicine tank 2 becomes smaller than an amount of the medicine to be administered per inhalation. For example, a function to count an ejection amount is provided in the body, and a remaining amount of the medicine can be calculated by such an ejection amount counting function. Accordingly, it is also possible to prompt the user to replace the ejection head section 1 and the medicine tank 2 by notifying the user of replacement timing, or not to perform the ejection until the replacement is completed. Reference numeral 31 denotes a protective cover for preventing the user from easily contacting an internal mechanism of the inhaler.

(Ejection Head Section and Medicine Tank)

Figure 3A:
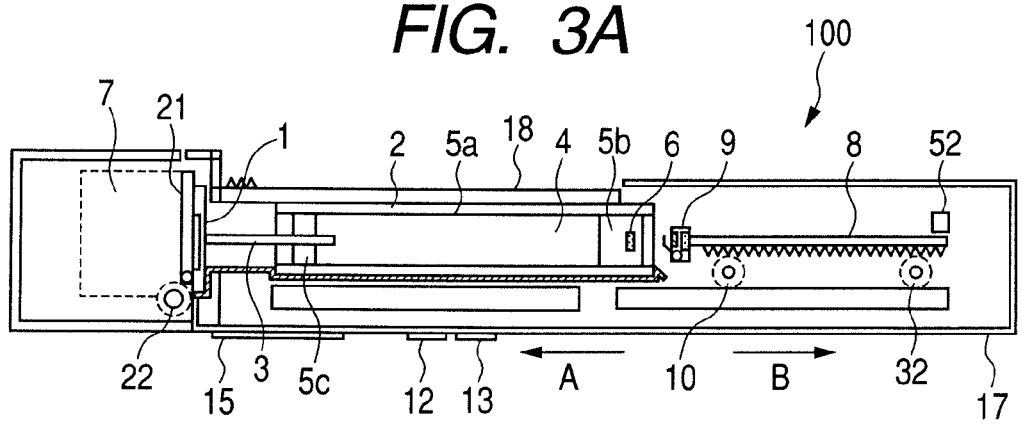
FIG. 3A is a cross-sectional view in which the medicine ejection device of FIG. 1 is cut along a cross section perpendicular to an air path 7.

FIG. 3A is a cross-sectional view in which the medicine ejection device of FIG. 1 is cut along a cross section perpendicular to the air path 7.

Figure 3B:
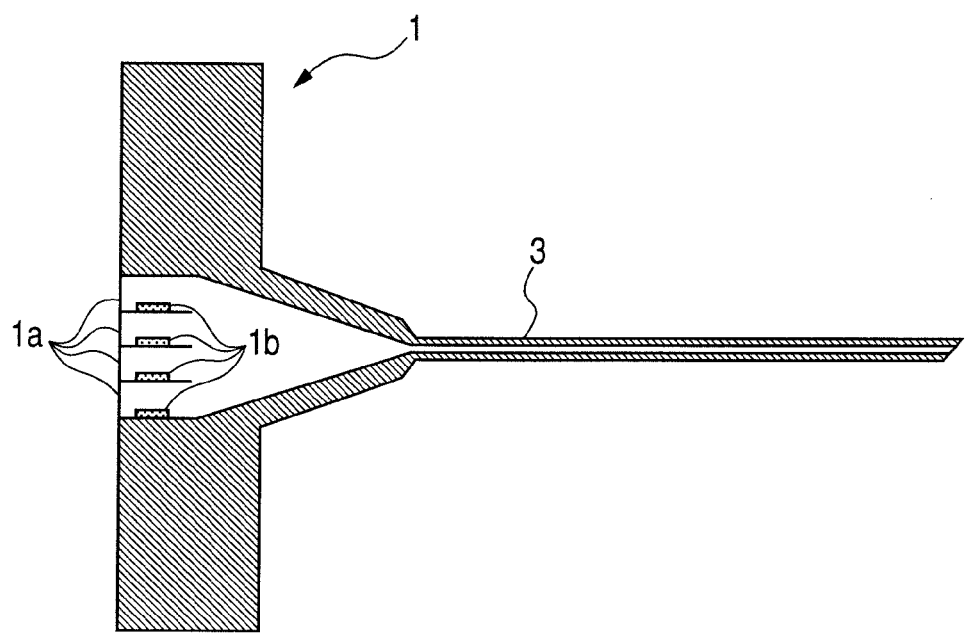
FIG. 3B is an enlarged view illustrating an ejection head section 1 of FIG. 3A.

As illustrated in FIG. 3B, the ejection head section 1 is formed of ejection nozzles 1a from which the medicine is ejected, and elements 1b which generate energy for ejecting the medicine from the nozzle 1a. Such ejection energy generation elements 1b impart the ejection energy to the medicine supplied from the medicine tank 2 through a communication duct 3. In such a way, the medicine is ejected from the ejection nozzles 1a.

Here, the medicine ejection section (ejection head) 1 includes the ejection nozzles 1a, and arbitrary ejection energy generation elements 1b provided in a one-to-one, one-to-many or many-to-one relationship with respect to the nozzles 1a. There can be exemplified an electrothermal transducer that imparts thermal energy to the medicine or an electromechanical transducer that imparts mechanical energy thereto. Specifically, as an ejection method for the medicine, there can be exemplified a method of imparting the thermal energy to the medicine by using the electrothermal transducer and ejecting the medicine (thermal-jet method), and a method of ejecting the medicine by using a vibration pressure of the electromechanical transducer (for example, piezoelectric element) that imparts the mechanical energy to the medicine (piezo-jet method). Those methods are sometimes called inkjet methods. The ejection method is selectable in accordance with a type of the medicine.

In the case of using the thermal-jet method, for each ejection head, it is possible to enhance size accuracy and reproducibility of a diameter of the nozzles, an amount of heat of a heat pulse for use in the ejection, a micro heater as the electrothermal transducer, and the like. Therefore, a narrow distribution of liquid droplet diameters can be achieved. Further, manufacturing cost of the head is low, and the thermal-jet method is also highly applicable to a compact device in which it is necessary to frequently replace the head. Hence, in the case where portability and convenience are required for the medicine ejection device, it is particularly desirable to adopt an ejection principle of the thermal-jet method.

The medicine tank 2 as the medicine container section that contains the medicine 4 to be ejected is coupled to the ejection head section 1, and is shielded from the outside air except at the nozzles 1*a*. Further, at the storage time when the medicine is not ejected, a head cap 21 as a protective member that protects the ejection head section 1 closes the nozzles 1*a*, and hence the inside of the medicine tank 2 is completely shielded from the outside.

Here, in this specification, that an inner pressure of the medicine tank is a negative pressure refers to that a pressure inside the medicine tank is lower than a pressure of the outside air. Meanwhile, that the inner pressure of the medicine tank is a positive pressure refers to that the pressure inside the medicine tank is higher than the pressure of the outside air.

The medicine tank 2 is formed of a container body 5*a* in which both ends thereof are opened, and members 5*b* and 5*c* which close both ends thereof. A plug 5*c* is fixed to the container body 5*a*, and allows penetration therethrough of the communication duct 3 that allows the ejection head section 1 and the medicine tank 2 to communicate with each other, thereby fixing the communication duct 3 thereto. Further, a plug 5*b* functions as a movable wall that positionally shifts so that a capacity of the medicine tank 2 can increase and decrease, that is, can change in accordance with a predetermined pressure difference between the inside and outside of the medicine tank 2. In this embodiment, this predetermined pressure difference depends on the maximum static friction between the plug 5*b* as the movable wall and the container body 5*a*. When the pressure in the medicine tank 2 is the negative pressure, and force applied to the plug 5*b* by this negative pressure exceeds the maximum static friction, the plug 5*b* moves inward of the container so as to reduce the capacity of the medicine tank 2. Meanwhile, when the pressure in the medicine tank 2 is the positive pressure, and force applied to the plug 5*b* by this positive pressure exceeds the maximum static friction in a similar way, the plug 5*b* moves outward of the container so as to increase the capacity of the medicine tank 2. As the container body 5*a*, a glass container having rigidity can be exemplified. Further, as a material of the plugs 5*b* and 5*c*, butyl rubber and isoprene rubber can be exemplified.

FIG. 3A illustrates a state where the access cover 18 is closed. In the case of opening the access cover 18 as illustrated in FIG. 2, it is read in FIG. 3A that the access cover 18 is housed in the inside of the body of the inhaler 100. Here, though not shown in FIG. 3A, a plug 5*b*-side end portion of the container body 5*a* may be provided with a stopper so as to become an opening portion having a smaller diameter than an outer diameter of the plug 5*b*. In such a way, the plug 5*b* does not inappropriately fall off the container body 5*a*, and hence safety is enhanced.

The medicine for use in the present invention is a concept including not only medicine of a medicinal compound showing a pharmacological and physiological action but also a flavoring agent, a coloring agent, a pigment, and the like in addition thereto. Further, an arbitrary additive agent may be included in the concept of the medicine.

(Control for Inner Pressure of Tank Before Ejection)

Next, description is made of an example of a method of controlling the pressure in the medicine tank 2 before the medicine is ejected, such a pressure control method being a feature of the present invention, while referring to FIGS. 4A to 4E which schematically illustrate the medicine tank 2 and the like.

Figure 4A:
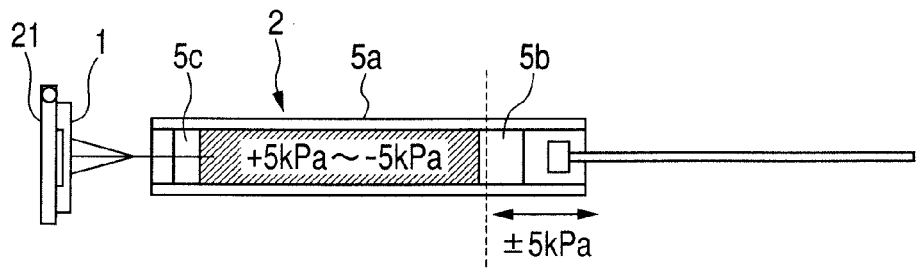
FIGS. 4A, 4B, 4C, 4D and 4E are schematic views illustrating an example of a pressure control method in a medicine tank 2 before ejection, the pressure control method being a feature of the present invention.

FIG. 4A: FIG. 4A illustrates a storage state where the ejection is not performed. Here, description is made on the premise that, when the difference between the pressure in the medicine tank 2 and the pressure of the outside air exceeds ±5 kPa, the plug 5*b* slidably moves with respect to the container body 5*a* so that the capacity of the medicine tank can increase or decrease. This threshold value is uniquely determined by the material and size of the container body 5*a* and the material and size of the plug 5*b*. In this case, by the fact that an outside air environment changes during the storage, the inner pressure in the medicine tank 2 becomes a positive pressure which is higher than the outside air pressure by 5 kPa at the maximum, and becomes a negative pressure which is lower than the outside air pressure by 5 kPa at the minimum. However, when the head cap 21 as the protective member that protects the nozzles is opened and the ejection is started in this state, there is a risk that the pressure in the medicine tank 2 may be the positive pressure, which is not desirable. This is because, when the pressure in the medicine tank 2 is the positive pressure, not only appropriate ejection cannot be performed, but also in some cases, the medicine may leak from the nozzles when the head cap is opened.

Figure 4B:
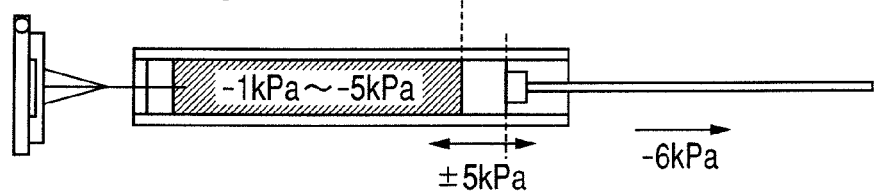

FIG. 4B: In this context, before opening the head cap 21, pressure control is performed so as to surely set the inside of the medicine tank 2 at the negative pressure. Here, in order that the inner pressure of the container can vary to the negative pressure direction equivalent to −6 kPa, the plug 5*b* is moved so that the capacity of the medicine tank can increase. In such a way, even if the inside of the container is in a positive pressure state of +5 kPa as the maximum, the inside of the container can be surely set at the negative pressure. Meanwhile, if the inside of the container is in a negative pressure state of −5 kPa as the minimum, the inside of the container temporarily turns to a negative pressure state of −11 kPa immediately after the plug 5*b* is moved. However, the negative pressure of −11 kPa in this case exceeds a movement threshold value of the plug 5*b*, and hence the plug 5*b* moves toward the inside of the container. Then, the movement of the plug 5*b* is stopped when the inner pressure of the container returns to the negative pressure state of approximately −5 kPa. Specifically, regardless of a value of the inner pressure of the container when the container preserves the medicine, the inner pressure of the container before the ejection can be surely set within a range of −1 to −5 kPa by the above-mentioned operations.

Specifically, it is important to generate pressure variations toward the negative pressure direction, which have a larger value than a value equivalent to the predetermined pressure difference (movement threshold value) at which the movement of the plug 5*b* as the movable wall is started. In such a way, the inner pressure of the container before the ejection can be surely set in a state where the pressure is negative, and becomes free from an excessive negative pressure state.

Note that a movement amount of the plug 5*b* and the pressure change in the container are uniquely determined by a container volume at that time, and hence a table for determining the movement amount based on a volume of the container before use thereof can be provided in a control section.

Figure 4C:
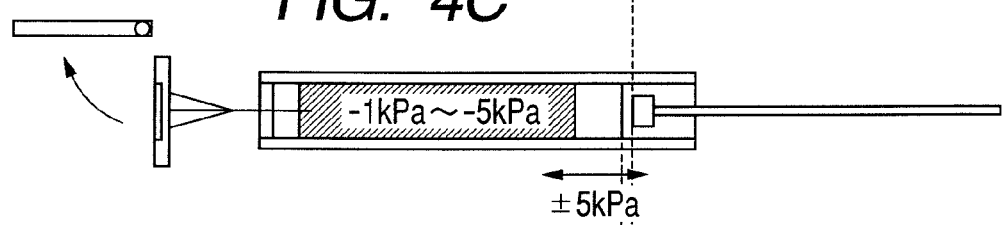

FIG. 4C: The head cap 21 is opened, and preparation to start the ejection is performed. Here, the pressure inside of the medicine tank 2 is surely the negative pressure, and there is no risk that the medicine may leak from the nozzles.

Figure 4D:
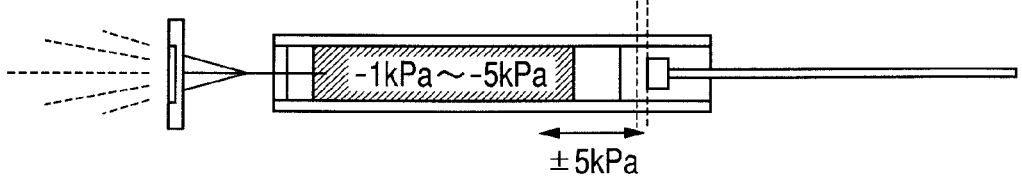

FIG. 4D: The ejection energy generation elements 1*b* are driven to eject a medicine 4. In the above-mentioned inhalation device, the ejected medicine can be administered to the user by allowing the user to inhale the medicine. During the ejection, the medicine contained in the medicine tank 2 decreases, whereby the inner pressure of the container varies to the negative pressure direction. Accordingly, the plug 5b is left apart from a drive axis 8 without being connected thereto so that the predetermined inner pressure can be maintained. In such a way, the plug 5b is set in a state of being slidably movable with respect to the container body 5a so that the capacity of the medicine tank can decrease when the negative pressure in the medicine tank 2 exceeds −5 kPa. As a result, even if the inner pressure of the container momentarily goes out of the range of −1 to −5 kPa, the inner pressure remains within the range of −1 to −5 kPa after elapse of a predetermined time.

Figure 4E:
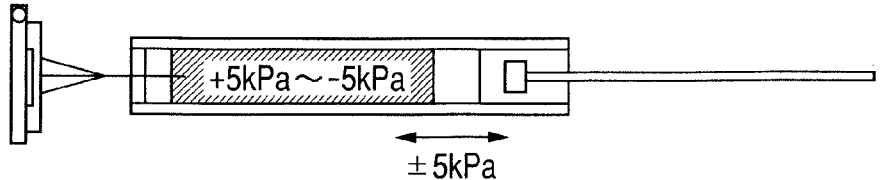

FIG. 4E: After a predetermined dosage is ejected, the head cap 21 is closed, and the inhalation device enters a storage mode of protecting the nozzles.

(Pressure Control Unit)

Figure 3C:
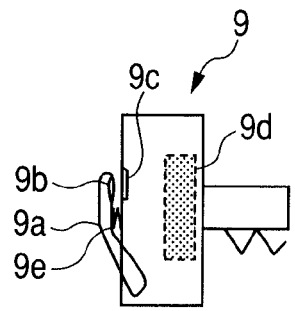
FIG. 3C is an enlarged view illustrating a sensing section 9 of FIG. 3A.

Here, referring to FIGS. 3A and 3C, description is made of pressure control unit for realizing the above-mentioned pressure control in this embodiment. FIG. 3C illustrates a configuration of a plug sensing/absorbing section 9 in an enlarger manner. The pressure control unit in the present invention is a mechanism that moves the plug 5b before the ejection.

Figure 5:
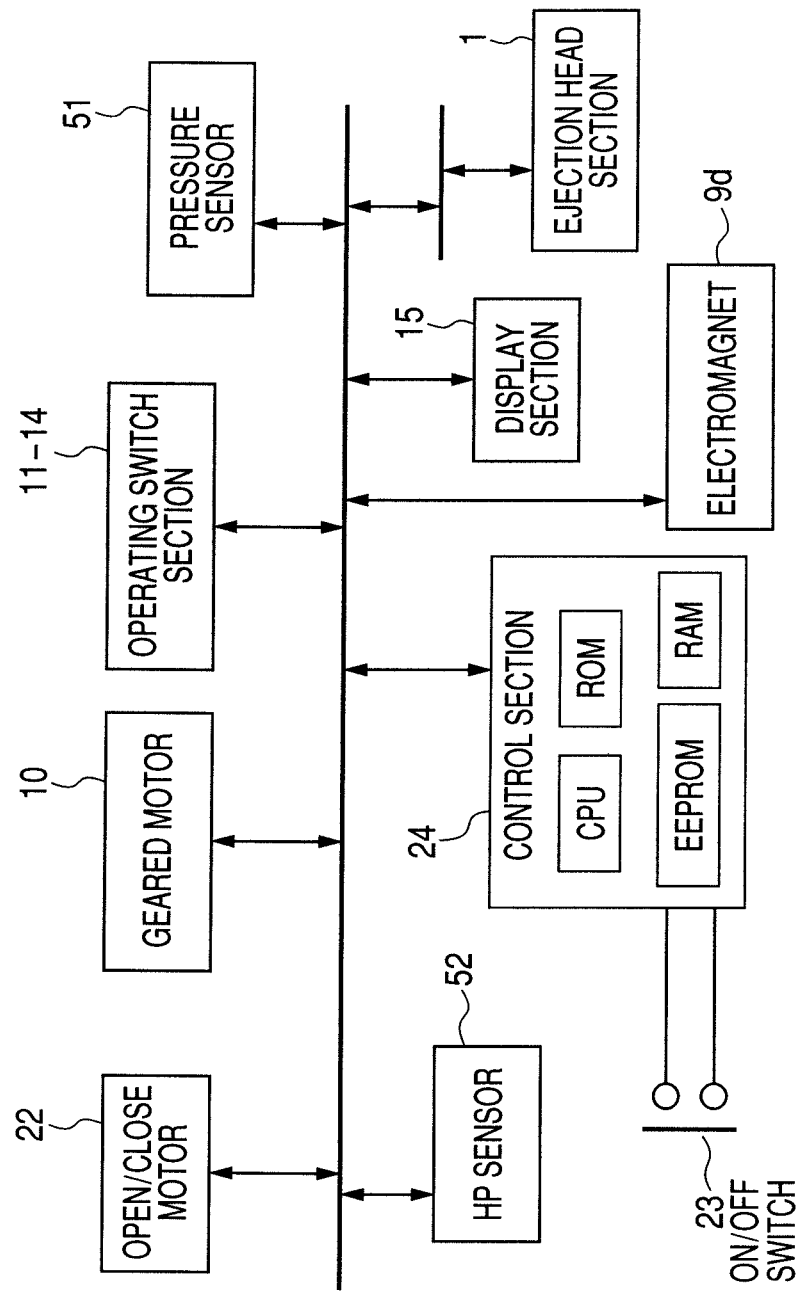
FIG. 5 is an electric configuration diagram of the medicine ejection device illustrated in FIG. 1, FIG. 2, and FIGS. 3A, 3B and 3C.

In the storage state (FIG. 4A) where the ejection is not performed, an electromagnet 9d of the plug sensing/absorbing section 9 attached onto a tip end of the drive axis 8 is in an OFF state. The plug 5b and the plug sensing/absorbing section 9 are placed at an interval of 5 mm by controlling rotation of a geared motor 10. The control for the geared motor 10 is performed by a control section 24 (FIG. 5). Every time when a current position of the drive axis 8 changes, the control section 24 stores the position in an EEPROM. When there occurs a necessity to confirm the position in terms of the control, the control section 24 reads out information on the position, and controls the geared motor 10. In such a way, the electromagnet 9d is left in the OFF state, and hence an armature 6 in the plug 5b and the plug sensing/absorbing section 9 do not pull each other. Hence, when the difference between the pressure in the medicine tank 2 and the pressure of the outside air exceeds ±5 kPa, the plug 5b slidably moves with respect to the container body 5a so that the capacity of the medicine tank can increase or decrease.

Next, a specific configuration for realizing the pressure control step illustrated in FIG. 4B is described. In FIG. 3A, the drive axis 8 is supported by two gears which are a guide gear 32 and a gear attached to a rotation axis of the geared motor 10. In the event of performing the pressure control for the inside of the medicine tank 2, the control section 24 drives the geared motor 10, and moves the drive axis 8 in a direction A. A sensing lever 9a is provided on an extreme tip end portion of the plug sensing/absorbing section 9, in which the plug sensing/absorbing section 9 contacts the plug 5b, and an electrical connection portion 9b is provided in an inside of the sensing lever 9a. When the plug sensing/absorbing section 9 contacts the plug 5b, a spring 9e provided between the sensing section 9 and the lever 9a is compressed, whereby the electrical connection portion 9b contacts an electrical connection portion 9c on the sensing section 9 side. The control section 24 senses such electrical conduction, and thereby senses that the sensing section 9 has contacted the plug 5b.

Thereafter, the control section 24 switches on the electromagnet 9d, and fixes and couples the plug 5b and the drive axis 8 (plug sensing/absorbing section 9) to each other by attraction force between the electromagnet 9d and the armature 6. In this state, the control section 24 drives the geared motor 10, and moves the plug 5b by a predetermined amount in a direction B. Thereafter, the control section 24 switches off the electromagnet 9d, moves the drive axis 8 in the direction B by the geared motor 10, and separates the plug sensing/absorbing section 9 and the plug 5b from each other. In such a way, the plug 5b is released from the drive axis 8, and becomes free. In the case where the inner pressure of the medicine tank 2 is lower than −5 kPa at this time, the plug 5b moves in the direction A. In such a way, the inner pressure of the container before the ejection can be set within the range of −1 to −5 kPa.

In the cap opening step illustrated in FIG. 4C and in the step of entering the storage mode of FIG. 4E, the control section 24 controls rotation of a motor 22, and opens/closes the head cap 21.

FIG. 5 illustrates an electric configuration diagram of the medicine ejection device illustrated in FIG. 1, FIG. 2, and FIGS. 3A to 3C. Reference numeral 1 denotes the ejection head. Reference numeral 10 denotes the geared motor capable of moving the drive axis 8 illustrated in FIG. 3A in the direction A or the direction B. Reference numerals 11 to 14 denote a variety of operating switches. Reference numeral 15 denotes a liquid crystal display section that displays information for operating this device illustrated in FIG. 1. Reference numeral 22 denotes a motor that controls open/close of the head cap 21 that hermetically caps surfaces of the nozzles of the ejection head 1. Reference numeral 23 denotes a switch that controls ON/OFF of a power supply supplied to an electric circuit of this device. Reference numeral 24 denotes the control section that controls the electric circuit of this device. The control section 24 includes a non-volatile memory (EEPROM) that stores the newest information as to the position that the drive axis 8 is controlled to locate at present, and the like. Reference numeral 51 denotes a pressure sensor that is arranged in the air path 7 and is capable of sensing the negative pressure generated in the air path when the user starts the inhalation. Reference numeral 52 denotes a sensor for sensing a home position detectable when the drive axis 8 goes away from the plug 5b to the maximum extent. The drive axis 8 is controlled based on the position detected by this sensor.

(Usage Example of Inhalation Device)

Figure 6:
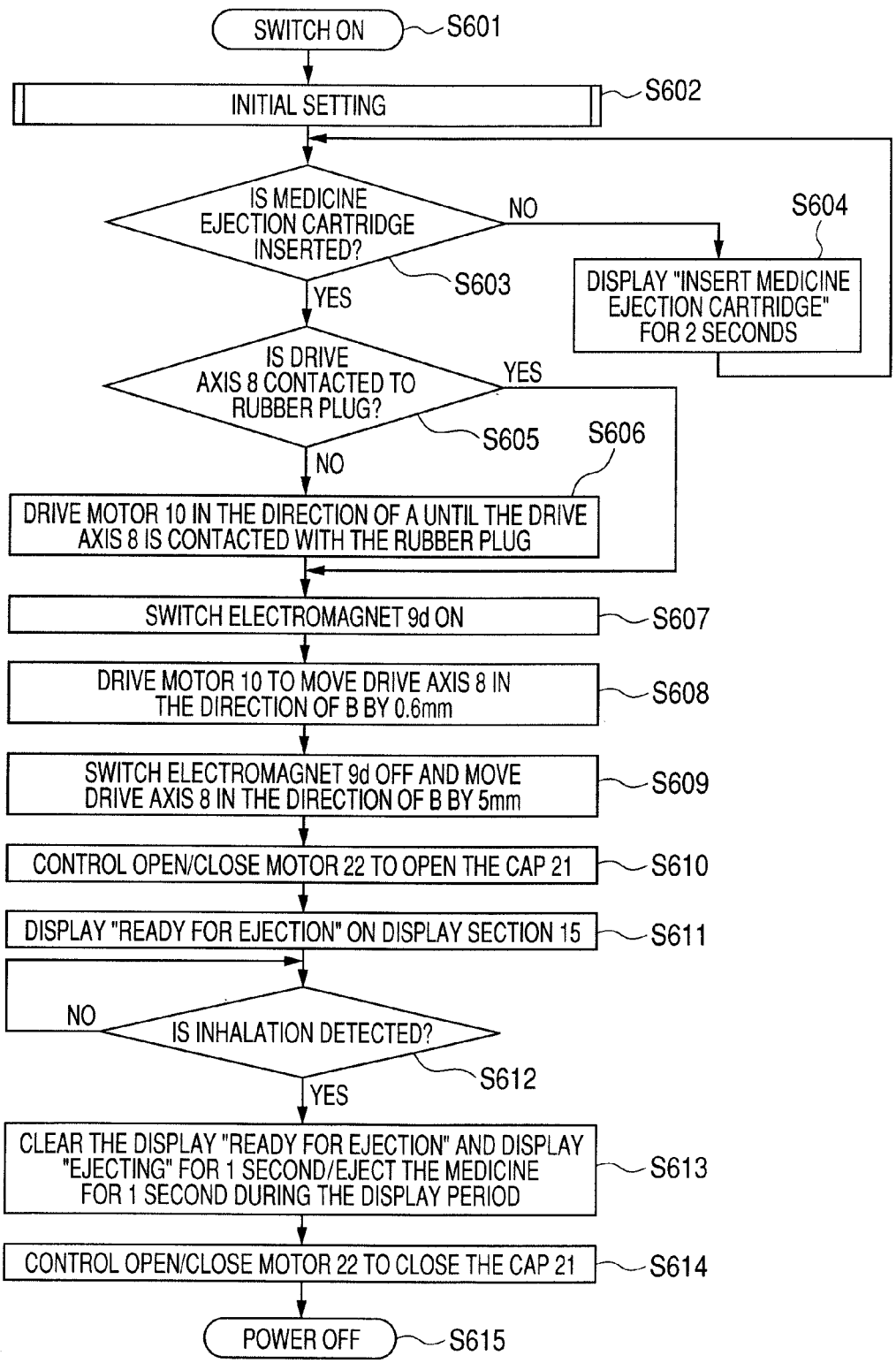
FIG. 6 is a flowchart illustrating a usage example of the inhalation device.

Description is made of a usage example of the inhalation device along a flowchart illustrated in FIG. 6.

When the user presses the ON/OFF switch 23, the control section 24 senses this action, and turns on the power supply of the entire inhalation device (S601). Thereafter, the control section 24 makes an initial setting of the inhalation device (S602). At the initial setting, the control section 24 reads a value of the pressure sensor 51, and stores this value as a value at which it is determined that the inhalation is not performed in the event of sensing the inhalation on and after. The ejection head section 1 and the medicine tank 2 are detachable from the inhalation device, and hence the control section 24 judges whether or not those are inserted (S603), and displays such display saying "Insert medicine ejection cartridge" on the display section 15 for two seconds in the case where those are not inserted (S604).

In the case where it is judged that the ejection head section 1 and the medicine tank 2 are inserted, the control section 24 executes routine processing for preparing to open the head cap 21 as described later. First, the control section 24 electrically judges whether or not the sensing lever 9 is in contact with the plug 5b (S605). In the case where the sensing lever 9 is not in contact with the plug 5b, the control section 24 drives the geared motor 10 until such contact is sensed so that the drive axis 8 can move in the direction A (S606). The control section 24 switches on the electromagnet 9d in a state where the above-mentioned contact is sensed (S607). The electromagnet 9d is switched on by the control section 24, whereby the plug 5b and the drive axis 8 are integrated with each other by attraction force between the armature 6 and the electromagnet 9d. Thereafter, the control section 24 drives the geared motor 10 so that the drive axis 8 can move by 0.6 mm in the direction B (S608). In this usage example, the material of the container 5a is glass, an inner diameter thereof is 6.5 mm and a length thereof is 45 mm. The material of the plug 5b is butyl rubber, and an outer diameter thereof is 6.65 mm. In the case where an experiment was carried out under such conditions, the movement threshold value became approximately ±5 kPa. Further, an initial capacity of the medicine tank was 1 ml, and it was obtained that pressure variations of −6 kPa occurred by moving the plug 5b by 0.6 mm. Accordingly, the plug 5b was moved by the above-mentioned value.

Thereafter, the electromagnet 9d is switched off, and the drive axis 8 is moved in the direction B by 5 mm, whereby the drive axis 8 is pulled apart from the plug 5b (S609). Next, the control section 24 drives the motor 22 to open the head cap 21 (S610). In such a way, ejection preparation is completed, and hence such display saying "Ready for ejection" is displayed on the display section 15 (S611). As described above, it is desirable that, in the pressure control method of the present invention, the pressure variations are generated in response to opening timing of the head cap 21 before starting the inhalation. For example, when the user turns on the power supply of the inhalation device as described above, it may be judged that the inhalation is to be performed, and then the sequential pressure control may be performed. Further, only that the power supply has been turned on does not always indicate that the user desires the inhalation, and hence another routine processing in which the device enters an inhalation mode may be provided separately. As described above, in the case where there arises a necessity to open the head cap 21, it is desirable to perform the pressure control corresponding to the opening timing thereof.

Next, when the inhalation by the user is sensed (S612), the ejection energy generation elements 1b are driven under predetermined conditions, whereby the medicine is ejected (S613). Note that such sensing of the inhalation can be realized by detecting a pressure change caused in the air path 7 by the inhalation by the user, for example, if the pressure sensor 51 is provided in the air path 7.

After the ejection is ended, the control section 24 controls the motor 22 to close the head cap 21 (S614). Finally, the power supply is turned off, and the processing proceeds to the storage state (S615).

In such a way, the inner pressure of the container can be surely set at the negative pressure state within the fixed range before the ejection, and hence stable ejection can be realized from the initial period of the ejection.

(Second Embodiment of Pressure Control Unit)

Next, description is made of a second embodiment of the unit for controlling the inner pressure of the container. In the first embodiment, the plug 5b as the movable wall is slidably movable, and hence the plug 5b is pulled in the outward direction of the container, whereby the inner pressure of the container is lowered. In this embodiment, the capacity of the inside of the container is increased by the plug 5c that fixes the communication duct 3 thereto, whereby the inner pressure is lowered.

For example, the plug 5c is also designed so as to be slidable with respect to the container, and the container body 5a is retreated prior to opening the head cap (movement in the direction B in FIG. 3A). It is not desirable that the communication of the medicine tank 2 with the ejection head be released, and hence it is desirable that a positional relationship between the communication duct 3 and the plug 5c be fixed. In this context, the container body 5a is moved, whereby the plug 5c is relatively slid with respect to the container 5a, and the capacity of the container can be increased. As a unit for moving the container 5a, there can be mentioned a unit in which a jig that fixedly supports the container 5a is provided, and the jig itself is moved by a rack and pinion mechanism or a jack mechanism.

(Third Embodiment of Pressure Control Unit)

Next, description is made of a third embodiment of the unit for controlling the inner pressure of the container.

Figure 7A:
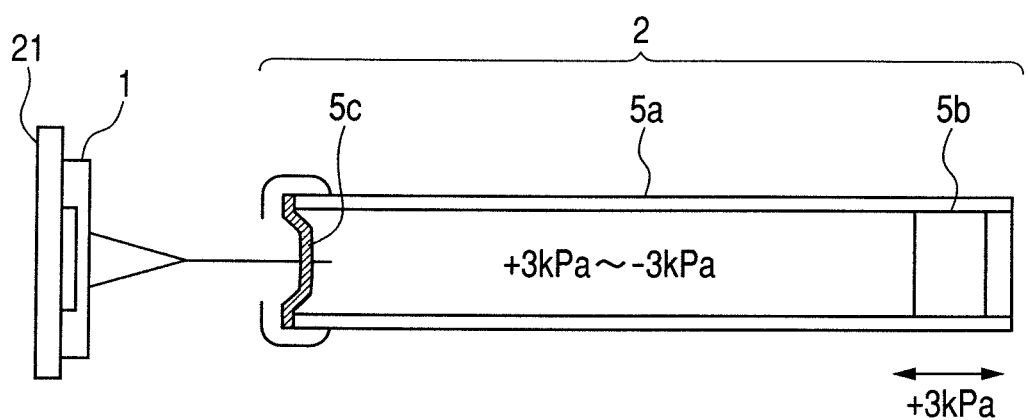
FIGS. 7A and 7B are schematic views illustrating a third embodiment of pressure control unit of the present invention.

FIG. 7A: FIG. 7A shows a storage state where the ejection is not performed. Here, description is made on the premise that the plug 5b slidably moves with respect to the container body 5a so that the capacity of the medicine tank can increase or decrease when the difference between the pressure inside the medicine tank 2 and the pressure of the outside air exceeds ±3 kPa. Such a threshold value is uniquely determined by the material and size of the container body 5a and the material and size of the plug 5b. In this case, by the fact that the outside air environment changes during the storage, the inner pressure of the medicine tank 2 becomes a positive pressure higher than the outside air pressure by 3 kPa at the maximum, and becomes a negative pressure lower than the outside air pressure by 3 kPa at the minimum. However, there is a possibility that, when the head cap 21 as the member that protects the nozzles is opened and the ejection is started in this state, the pressure in the medicine tank 2 may be the positive pressure, which is not desirable. This is because, when the pressure in the medicine tank 2 is the positive pressure, not only the appropriate ejection cannot be performed, but also it is apprehended that, in some cases, the medicine may leak from the nozzles when the head cap is opened.

Figure 7B:
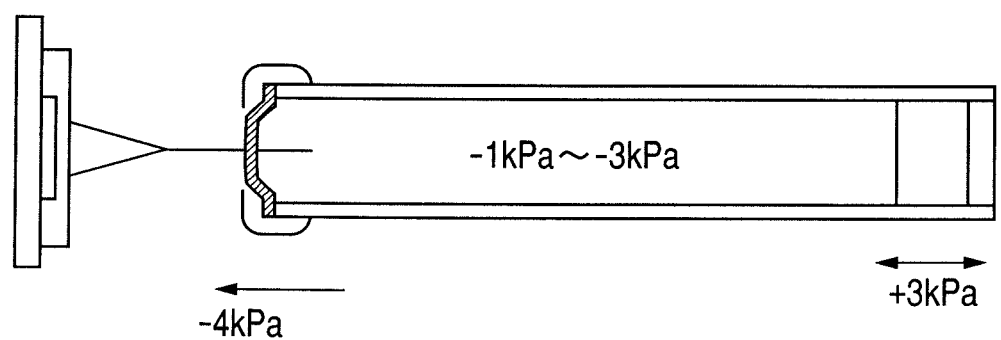

FIG. 7B: In this context, before opening the head cap, the pressure control is performed so as to surely set the inside of the medicine tank 2 at the negative pressure. Here, in order that the inner pressure of the container can vary to the negative pressure direction equivalent to −4 kPa, the plug 5c is curved so that the capacity of the medicine tank can increase. In such a way, even if the inside of the container is in a positive pressure state of +3 kPa as the maximum, the inside of the container can be surely set at the negative pressure. Meanwhile, if the inside of the container is in a negative pressure state of −3 kPa as the minimum, the inside of the container temporarily turns to a negative pressure state of −7 kPa immediately after the plug 5c is curved so that the capacity of the container body 5a can increase in the same way. However, the negative pressure of −7 kPa in this case exceeds the movement threshold value of the plug 5b, and hence the plug 5b moves toward the inside of the container. Then, the movement of the plug 5b is stopped when the inner pressure of the container returns to the negative pressure state of approximately −3 kPa. Specifically, regardless of the value of the inner pressure of the container when the container preserves the medicine, the inner pressure of the container before the ejection can be surely set within a range of −1 to −3 kPa by the above-mentioned operations.

Specifically, it is important to generate the pressure variations toward the negative pressure direction, which have a larger value than a value equivalent to the predetermined pressure difference (movement threshold value) at which the movement of the plug 5b as the movable wall is started. In such a way, the inner pressure of the container before the ejection can be surely set in the normal state where the pressure is negative, and becomes free from the excessive negative pressure state.

Note that a curved amount of the plug 5c and the pressure change in the container are uniquely determined by a container volume at that time, and hence a table for determining the curved amount based on the volume of the container before use thereof can be provided in the control section.

The medicine ejection device of the present invention is usable for a variety of purposes besides that for inhaling the medicine. For example, the medicine ejection device is usable as a spray ejection device of an air freshener or the like, an inhalation device of a delicacy item such as nicotine, and the like. As described above, the medicine ejection device of the present invention is applicable to a variety of purposes which require sure and sanitary ejection.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2008-069720, filed Mar. 18, 2008, which is hereby incorporated by reference herein in its entirety.

The invention claimed is:

1. A medicine ejection device comprising:
   a medicine ejection section including ejection nozzles and an element that generates energy for ejecting medicine from said ejection nozzles;
   a medicine container section that is coupled to said medicine ejection section and contains the medicine, said medicine container section including a container body and a movable wall, and wherein said movable wall moves in relation to said container body so that a capacity of said medicine container section can change in accordance with a predetermined pressure difference between the inside and outside of said medicine container section; and
   a pressure control unit configured to generate pressure variations in a negative pressure direction inside said the medicine container section, wherein said pressure control unit applies a force on said movable wall before ejection of the medicine from said ejection nozzles and releases the force from said movable wall when ejecting the medicine, the force being more than a maximum static friction between said container body and said movable wall of said medicine container section.

2. A medicine ejection device according to claim 1, wherein said element comprises one of an electrothermal transducer that imparts thermal energy to the medicine, and an electromechanical transducer that imparts mechanical energy to the medicine.

3. A medicine ejection device according to claim 1, further comprising a protective member that protects said ejection nozzles,
   wherein said pressure control unit releases the force in response to opening timing of said ejection nozzles by said protective member.

4. A medicine ejection device according to claim 1, wherein said pressure control unit is configured to release the force from said movable wall.

* * * * *